(12) United States Patent
Kunugiza et al.

(10) Patent No.: US 7,595,301 B2
(45) Date of Patent: Sep. 29, 2009

(54) STAPLE TYPE OLIGONUCLEOTIDE AND DRUG COMPRISING THE SAME

(75) Inventors: Yasuo Kunugiza, Suita (JP); Naruya Tomita, Osaka (JP); Hideo Hashimoto, Osaka (JP); Hideki Yoshikawa, Toyonaka (JP); Ryuichi Morishita, Suita (JP)

(73) Assignee: Anges MG, Inc., Osaka (JP)

( * ) Notice: Subject to any disclaimer, the term of this patent is extended or adjusted under 35 U.S.C. 154(b) by 280 days.

(21) Appl. No.: 10/568,226

(22) PCT Filed: Sep. 29, 2004

(86) PCT No.: PCT/JP2004/014694

§ 371 (c)(1),
(2), (4) Date: Feb. 14, 2006

(87) PCT Pub. No.: WO2005/030960

PCT Pub. Date: Apr. 7, 2005

(65) Prior Publication Data

US 2006/0276421 A1 Dec. 7, 2006

(30) Foreign Application Priority Data

Sep. 30, 2003 (JP) .............................. 2003-341419

(51) Int. Cl.
*A61K 48/00* (2006.01)
*A61K 31/70* (2006.01)
*C07H 21/02* (2006.01)
*C07H 21/04* (2006.01)

(52) U.S. Cl. ..................... 514/44; 536/24.1; 536/24.5

(58) Field of Classification Search ....................... None
See application file for complete search history.

(56) References Cited

FOREIGN PATENT DOCUMENTS

| WO | WO 9219732 A1 | * 11/1992 |
|----|---------------|-----------|
| WO | WO 94/12633   |   6/1994  |
| WO | WO 94/23026   | * 10/1994 |

OTHER PUBLICATIONS

Ahn et al. 2002, Gene Therapy, vol. 9, No. 24, pp. 1682-1692.*
Jen et al. Stem Cells, 2000, vol. 18, pp. 307-319.*
Caplen et al. Geen 2000, vol. 252, pp. 95-105.*
Caplen 2003, Expert. Opin. Biol. Ther. vol. 3, pp. 575-586.*

International Search Report for PCT/JP2004/014694 dated Nov. 16, 2004.
Shibuya et al., *A double-strand decoy DNA oligomer for NF-κB inhibits TNFα-induced ICAM-1 expression is sinusoidal endothelial cells,* Biochem. Biophys. Res. Commun., 2002, vol. 298, pp. 10-16.
Novina et al., *siRNA-directed inhibition of HIV-1 infection,* Nat. Med., 2002, vol. 8, No. 7, pp. 681-686 and one page errata and corrigenda.
Park et al., *Inhibitory effects of novel E2F decoy oligodeoxynucleotides on mesangial cell proliferation by coexpression of E2F/DP,* Biochem. Biophys. Res. Commun., 2003, vol. 308, No. 4, pp. 689-697.
Ahn et al., *Novel E2F decoy oligodeoxynucleotides inhibit in vitro vascular smooth muscle cell proliferation and in vivo neointimal hyperplasia,* Gene Ther., 2002, vol. 9, No. 24, pp. 1682-1692.
Ahn et al., *Inhibitory Effects of Novel AP-1 Decoy Oligodeoxynucleotides on Vascular Smooth Muscle Cell Proliferation in Vitro and Neointimal Formation* in Vivo, Circ Res., 2002, vol. 90, No. 12, pp. 1325-1332.
Supplementary Search Report for EP 04788459.8, five pages, dated May 4, 2009.
Clusel et al., Ex vivo regulation of specific gene expression by nanomolar concentration of double-stranded dumbbell oligonucleotides, Nucl. Acids Res., 1993, vol. 21, No. 15, pp. 3405-3411.
Hosoya et al., *Sequence-specific inhibition by circular dumbbell DNA oligonucleotides,* FEBS Lett., 1999, vol. 461, No. 3, pp. 136-140.
Lim et al., *Sequence-independent inhibition of RNA transcription by DNA dumbbells and other decoys,* Nucl. Acids Res., 1997, vol. 25, No. 3, pp. 689-697.

* cited by examiner

*Primary Examiner*—Janet L. Epps-Smith
(74) *Attorney, Agent, or Firm*—Nixon & Vanderhye P.C.

(57) ABSTRACT

Conventional oligonucleotides are opened at both ends and thereby unstable. Their stability against catabolic enzymes is increased by phosphorothioate modification, but such phosphorothioate causes toxicity. The present invention provides oligonucleotides and medicaments in which these problems are improved. That is, it provides staple oligonucleotides and medicaments containing the same as the active ingredient. Specifically, it provides transcription factor inhibitors, antisense oligonucleotides and siRNAs. More specifically, it provides agents for preventing, treating or improving inflammation, autoimmune diseases, central diseases, reperfusion injury in ischaemic diseases, worsened prognosis after organ transplantation or organ surgery, or restenosis after PTCA. Further specifically, it provides agents for preventing, treating or improving arthritis, dermatitis, nephritis, hepatitis, renal failure, cystitis, prostatitis, urethritis, ulcerative colitis, Crohn disease, chronic rheumatoid arthritis, osteoarthritis, atopic dermatitis, contact dermatitis, psoriasis, cutaneous ulcer or decubitus.

3 Claims, 3 Drawing Sheets

Tolerance test of staple decoy in synovial fluid as intact synovial fluid: 0 50 100 %   0 50 100 %   0 50 100 %   0 50 100 %                    0 50 100 %
molecular-weight marker   1) A B C   2) D E F   3) G H I   4) J K L   molecular-weight marker   5) M N O 1) phosphorothioated double-stranded decoy    2) phosphorothioated staple decoy 3) non-phosphorothioated staple decoy    4) single-stranded decoy 5) phosphorothioate-terminated single-stranded decoy

SEQUENCE LISTING

<160> NUMBER OF SEQ ID NOS: 3

<210> SEQ ID NO 1
<211> LENGTH: 48
<212> TYPE: DNA
<213> ORGANISM: Artificial Sequence
<220> FEATURE:
<223> OTHER INFORMATION: Synthetic DNA

<400> SEQUENCE: 1
atttccctcc aaaaggaggg aaatcccttc aaggaaaacc ttgaaggg                48

<210> SEQ ID NO 2
<211> LENGTH: 53
<212> TYPE: DNA
<213> ORGANISM: Artificial Sequence
<220> FEATURE:
<223> OTHER INFORMATION: Synthetic DNA

<400> SEQUENCE: 2
atttccctcc tggatcccag gagggaaatc ccttcaagga aaaccttgaa ggg          53

<210> SEQ ID NO 3
<211> LENGTH: 48
<212> TYPE: DNA
<213> ORGANISM: Artificial Sequence
<220> FEATURE:
<223> OTHER INFORMATION: Synthetic DNA

<400> SEQUENCE: 3
atttcccttt ttttaaaggg aaatcccttc aagatttttc ttgaaggg                48

STAPLE TYPE OLIGONUCLEOTIDE AND DRUG COMPRISING THE SAME

This is the U.S. national phase of Int'l Appln. No. PCT/JP2004/014694, filed 29 Sep. 2004, which designated the U.S. and claims priority benefit of JP 2003-341419, filed 30 Sep. 2003; the entire contents of each of which are hereby incorporated by reference.

TECHNICAL FIELD

The present invention relates to novel staple oligonucleotides, and medicaments comprising the same as the active ingredient.

BACKGROUND ART

Oligonucleotides have been widely used typically as transcription factor inhibitors, antisense oligonucleotides and siRNAs.

Of these, specific examples of the transcription factor inhibitors are molecular decoy nucleic acids (decoy oligonucleotide, hereinafter briefly referred to as "decoy") that specifically inhibit the activities of transcription factors regulating gene expression.

The "transcription" herein refers to a process in which a messenger RNA is synthesized using a DNA as a template upon in vivo expression of genetic information. A protein is then synthesized based on the information of the messenger RNA synthesized as a result of transcription. Factors regulating the transcription are designated as "transcription factors".

Specifically, fifty-four transcription factors such as NF-κB, STAT-1, STAT-2, STAT-3, STAT-4, STAT-5, STAT-6, GATA-3, AP-1, E2F, Ets and CRE are known.

Specific examples of the antisense oligonucleotides are medicaments each having a sequence paring with a target gene and inhibiting the expression of the gene.

Specific examples of siRNAs are medicaments inhibiting the expression of a target gene by RNA interference (RNAi).

These oligonucleotides structurally comprise double strands.

Background art to the present invention is documented in Biochem Biophys Res Commun. 2003 Sep. 5; 308(4):689-97, Gene Ther. 2002 Dec.; 9(24); 1682-92, and Circ Res. 2002 Jun. 28; 90(12):1325-32.

DISCLOSURE OF INVENTION

Problems to be solved by the present invention are that conventional oligonucleotides are opened at both ends and are thereby unstable, and that, when oligonucleotides are modified with phosphorothioate (S-modified) to elevate the stability against catabolic enzymes such as exonuclease, the phosphorothioate may cause toxicity.

Specifically, the present invention provides the following substances and medicaments.

(1) A staple oligonucleotide which is a single-stranded oligonucleotide comprising a 5'-end sequence, an intermediate sequence and a 3'-end sequence, the 5'-end sequence having a reverse complementarity with the intermediate sequence, the 3'-end sequence having a reverse complementarity with the intermediate sequence and the intermediate sequence having loops at both ends, the loops each comprising three to ten nucleotides and not forming a complementary bond intramolecularly.

(2) The staple oligonucleotide according to (1), wherein the single-stranded oligonucleotide has 30 to 70 nucleotides in length.

(3) The staple oligonucleotide according to (1) or (2), wherein the single-stranded oligonucleotide has 34 to 64 nucleotides in length.

(4) The staple oligonucleotide according to any one of (1) to (3), wherein the single-stranded oligonucleotide has 38 to 58 nucleotides in length.

(5) The staple oligonucleotide according to any one of (1) to (4), wherein the single-stranded oligonucleotide has 42 to 54 nucleotides in length.

(6) The staple oligonucleotide according to any one of (1) to (5), wherein the loops each have 4 to 6 nucleotides in length.

(7) The staple oligonucleotide according to any one of (1) to (6), wherein the single-stranded oligonucleotide has 42 to 54 nucleotides in length, and the loop has 4 to 6 nucleotides in length.

(8) The staple oligonucleotide according to any one of (1) to (7), wherein the oligonucleotide is a DNA or a DNA derivative.

(9) The staple oligonucleotide according to any one of (1) to (8), whose phosphate groups are not phosphorothioated.

(10) The staple oligonucleotide according to any one of (1) to (9), which is one selected from the group consisting of oligodeoxynucleotides of Sequence No. 1 to 3 of Sequence Listing.

(11) A medicament comprising the staple oligonucleotide of any one of (1) to (10).

(12) The medicament according to (11), which is a transcription factor inhibitor, an antisense oligonucleotide or an siRNA.

(13) The medicament according to (12), wherein the transcription factor inhibitor is an antagonistic inhibitor.

(14) The medicament according to (12) or (13), wherein the transcription factor is one selected from the group consisting of NF-κB, STAT-1, STAT-2, STAT-3, STAT-4, STAT-5, STAT-6, GATA-3, AP-1, E2F, Ets and CRE.

(15) The medicament according to any one of (12) to (14), which is an agent for preventing, treating or improving inflammation, an allergic disease, an autoimmune disease, a central disease, reperfusion injury in a ischaemic disease, worsened prognosis after organ transplantation or organ surgery or restenosis after percutaneous transluminal coronary angioplasty (PTCA).

(16) The medicament according to any one of (12) to (15), wherein the inflammation is arthritis, dermatitis, nephritis, hepatitis, renal failure, cystitis, prostatitis, urethritis, ulcerative colitis or Crohn disease.

(17) The medicament according to (16), wherein the arthritis is chronic rheumatoid arthritis or osteoarthritis.

(18) The medicament according to (16), wherein the dermatitis is atopic dermatitis, contact dermatitis, psoriasis, cutaneous ulcer or decubitus.

(19) Use of the staple oligonucleotide according to any one of (1) to (10), for producing a transcription factor inhibitor, an antisense or an siRNA.

(20) A method for preventing, treating or improving a disease against which a transcription factor inhibitor, an antisense or an siRNA is efficacious, the method comprises administering, to a patient, a pharmacologically effective amount of the staple oligonucleotide according to any one of (1) to (10).

The staple oligonucleotides according to the present invention are each a single-stranded oligonucleotide and have a staple-form structure (the shape of a staple after stapling) comprising a 5'-end sequence, an intermediate sequence and a 3'-end sequence, the 5'-end sequence having a reverse complementarity with the intermediate sequence, the 3'-end sequence having a reverse complementarity with the intermediate sequence and the intermediate sequence having loops at both ends, the loops each comprising three to ten nucleotides and not forming a complementary bond intramolecularly. More specifically, they have, for example, a structure represented by the following structural formula:

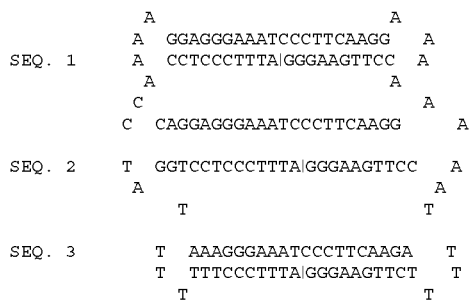

wherein the vertical lines mean a non-binding site (5' end and 3' end).

The staple oligonucleotides may have any base length not limited but generally comprise 30 to 70 nucleotides in length, preferably 34 to 64 nucleotides in length, more preferably 38 to 58 nucleotides in length, and further preferably 42 to 54 nucleotides in length.

The loops each comprise 3 to 10 nucleotides in length, and preferably 4 to 6 nucleotides in length.

The fold-back sequences at the 5' end and the 3' end (the sequences between the 5' end or the 3' end and the loop) can each have any base length but generally comprise 4 to 20 nucleotides in length, preferably 6 to 18 nucleotides in length, and more preferably 8 to 16 nucleotides in length.

The chain lengths of the fold-back sequences at the 5' end and the 3' end can be the same as (symmetric) or different from (asymmetric) each other.

Oligonucleotides according to the present invention are not limited, and can be any of DNAs, DNA derivatives, RNAs and RNA derivatives, of which DNAs or DNA derivatives are more preferred.

Specific examples of the staple oligonucleotides according to the present invention are oligodeoxynucleotides represented by Sequence No. 1 to 3 of Sequence Listing.

The staple oligonucleotides according to the present invention can be obtained by synthetically preparing the target single-stranded sequence according to a conventional procedure using, for example, a DNA synthesizer and heating the same in a solvent.

The term "phosphorothioate" in the present invention means a structure in which part or all of oxygen atoms in a phosphate group are replaced with sulfur atoms.

The staple oligonucleotides can be used as medicaments in any application. For example, they can be used as transcription factor inhibitors, antisense oligonucleotides and siRNAs. More specifically, they can be used as, for example, agents for preventing, treating or improving inflammation, an autoimmune disease, a central disease, reperfusion injury in a ischaemic disease, worsened prognosis after organ transplantation or organ surgery, or restenosis after PTCA.

Specific examples of the inflammation are arthritis, dermatitis, nephritis, hepatitis, renal failure, cystitis, prostatitis, urethritis, ulcerative colitis and Crohn disease.

The arthritis includes, for example, chronic rheumatoid arthritis (RA) and osteoarthritis (OA).

Specific examples of the dermatitis are atopic dermatitis, contact dermatitis, psoriasis, cutaneous ulcer and decubitus.

While the dose and administration route of the staple oligonucleotides according to the present invention vary depending on the type and severity of the disease, symptoms, age and sex of the patient, complications and concomitant drug, are not limited, and are generally administered at a dose of 10 μg to 10 g, preferably 100 μg to 5 g, and more preferably 1 mg to 1 g percutaneously, subcutaneously, intraarticularly, intramuscularly, intravenously or orally.

Apart from the present invention, there are cyclic decoys (dumbbell decoys) as disclosed in, for example, PCT International Publication Number WO 03/091432. However, the staple oligonucleotides according to the present invention each have a ring-opened site and are structurally fully different from them.

According to the present invention, the instability of conventional oligonucleotides is improved to thereby reduce doses and improve safety.

EXAMPLES

The present invention will be illustrated in further detail with reference to Examples below which by no means limit the scope of the present invention.

Example 1

Analysis of Anti-Inflammatory Effects of Staple Oligonucleotides

A. Quantitative Determination of Cytokine

1. Treatment of Synovial Tissue (1) the synovial tissue of a rheumatoid arthritis patient collected during operation was homogenized and inoculated (each 100 mg) onto a 24-well plate (serum free medium: 500 μl/well).

NF-κB decoy and scramble decoy were transfected (HVJ envelope method).

(2) Ultraviolet treatment was conducted at 99 mJ/cm$^2$ under the condition of HVJ 1.1×10$^4$ HAU/1.1 ml BSS (balanced salt solution (137 mM NaCl, 5.4 mM KCL, 10 mM Tris-HCl, pH 7.6).

(3) Each 1 ml was dispensed into 1.5-ml tubes and was centrifuged at 4° C. and 15000 rpm for 15 minutes.

(4) BSS was added to 200 μg of the decoy to make 92 μl.

(5) 3% Triton X-100/TE Buffer solution (8 μl) was added.

(6) After centrifuging at 4° C. and 15000 rpm for 15 minutes, the supernatant was removed.

(7) BSS (1 ml) was added and mixed, and the mixture was centrifuged at 15000 rpm for 15 minutes.

(8) After removing the supernatant, the residue was suspended in 200 μl of PBS.

(9) The decoy-HVJ envelope complex was added to the synovial tissue to 15 μM, followed by incubation in a $CO_2$ incubator at 37° C. for thirty minutes.

Sequences of Added Decoys

Double-stranded NE-κB decoy

5'-CCTTGAAGGGATTTCCCTCC-3'/5'-GGAGG-GAAATCCCTTCAAGG-3' (double strand of SEQ ID NOS: 4 and 5)

Scramble decoy
5'-CATGTCGTCACTGCGCTCAT-3'/5'-ATGAGCG-CAGTGACGACATG-3' (double strand of SEQ ID NOS: 6 and 7)

Staple oligonucleotide (i)
5'-ATTTCCCTCCAAAAGGAGGGAAATCCCT-TCAAGGAAAACCTTGAAGGG-3' (SEQ ID NO: 1 ligated at one point)

Dumbbell oligonucleotide (ii)
5'-ATTTCCCTCCAAAAGGAGGGAAATCCCT-TCAAGGAAAACCTTGAAGGG-3' (SEQ ID NO: 1 ligated at two points)

2. LPS Stimulation

(10) The decoy-HVJ envelope complex was removed, 500 μl of 10% FBS-containing culture medium was added, and LPS was added to 0.01 μg/ml.

3. Recovery of Cultured Mixture and Synovial Tissue and Determination of IL-1β

(11) Twenty-four hours later, the cultured mixture and synovial tissue were recovered. The synovial tissue was combined with 500 μl of PBS and homogenized using a homogenizer. After centrifuging at 5000 rpm for ten minutes, the supernatant was collected and then stored at −20° C. until the determination of IL-1β.

(12) The IL-1β levels of the culture supernatant and synovial supernatant were measured with the IL-1β ELISA Kit (ENDOGEN, Catalogue Number: EH21L1B).

4. Result

Figure 1:
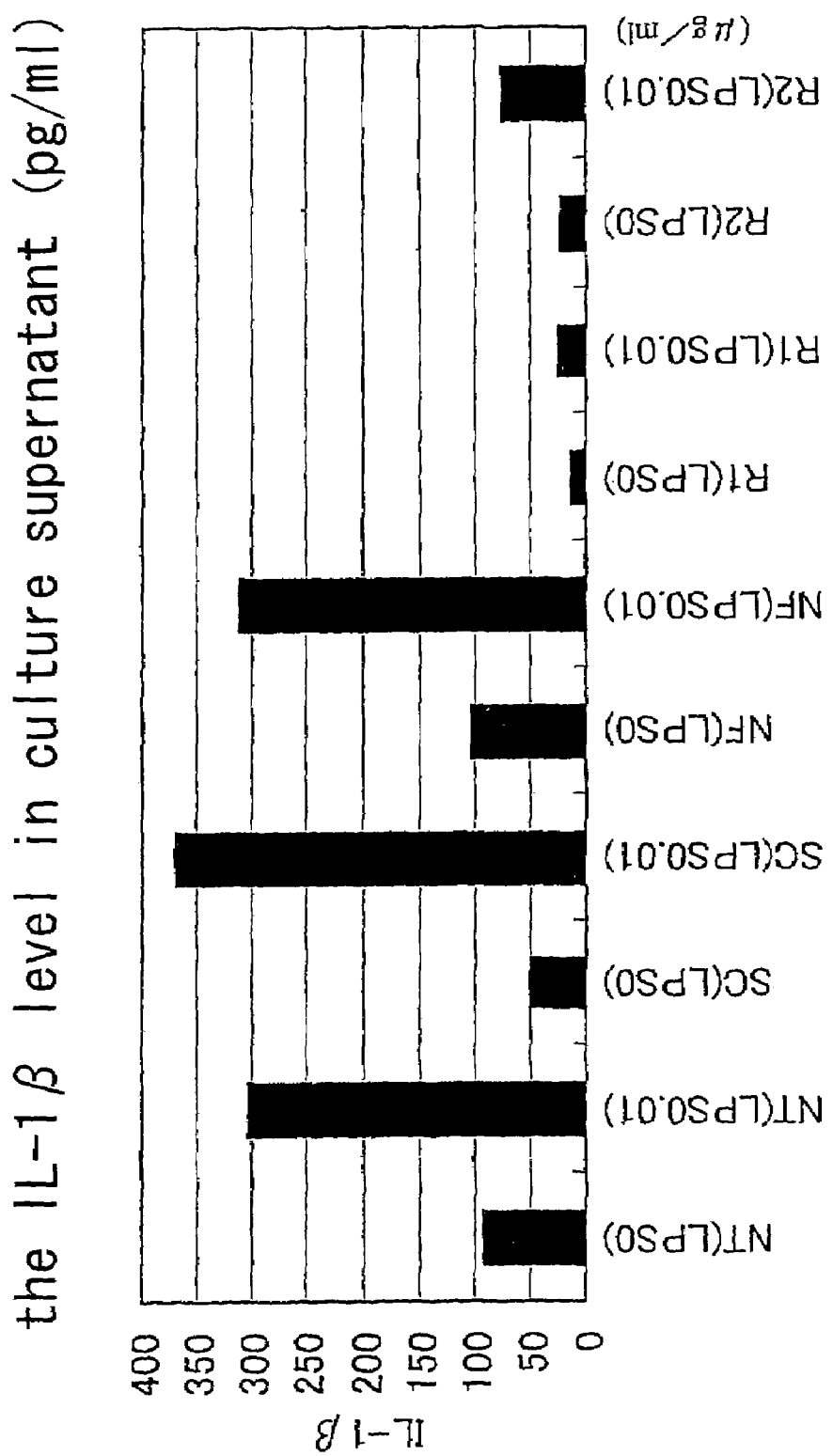
FIG. 1 is a graph showing the IL-1β level in culture supernatant twenty-four hours after LPS stimulation.

| IL-1β level in culture supernatant (pg/ml) (see FIG. 1) | | | |
|---|---|---|---|
| NT(LPS0) | 90.8 | NT(LPS0.01) | 303.9 |
| SC(LPS0) | 49.6 | SC(LPS0.01) | 370.7 |
| NF(LPS0) | 102.1 | NF(LPS0.01) | 312.6 |
| R1(LPS0) | 14.6 | R1(LPS0.01) | 25.1 |
| R2(LPS0) | 22.9 | R2(LPS0.01) | 74.3 |

Figure 2:
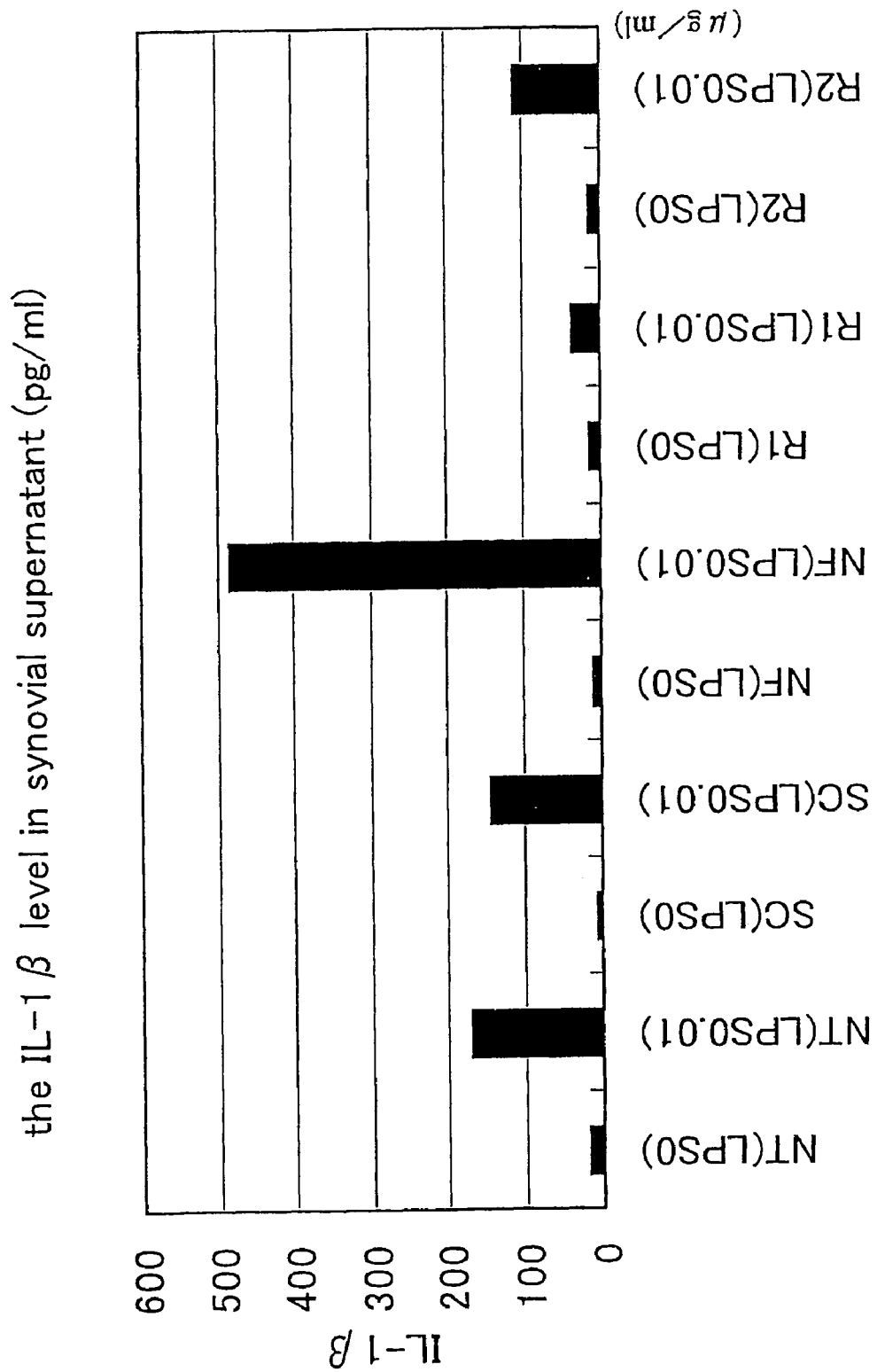
FIG. 2 is a graph showing the IL-1β level in synovial supernatant twenty-four hours after LPS stimulation.

| IL-1β level in synovial supernatant (pg/ml) (see FIG. 2) | | | |
|---|---|---|---|
| NT(LPS0) | 17.5 | NT(LPS0.01) | 170.9 |
| SC(LPS0) | 7.2 | SC(LPS0.01) | 145.7 |
| NF(LPS0) | 10.5 | NF(LPS0.01) | 484.8 |
| R1(LPS0) | 13.5 | R1(LPS0.01) | 38.9 |
| R2(LPS0) | 15.6 | R2(LPS0.01) | 111.2 |

NT: Untreated group
SC: Scramble decoy-administered group
NF: NFκB decoy-administered group
R1: Staple oligonucleotide (ligated at one point)
R2: Dumbbell oligonucleotide (ligated at two points)

In the staple oligonucleotide-administered group, the productions of IL-1β in the culture supernatant and the synovial supernatant were inhibited. The staple oligonucleotide ligated at one point showed a higher inhibitory effect (in this experiment, the double-stranded NFκB acting group showed a lower inhibitory effect).

The entire process of the quantitative determination of cytokine will be illustrated below.

Process

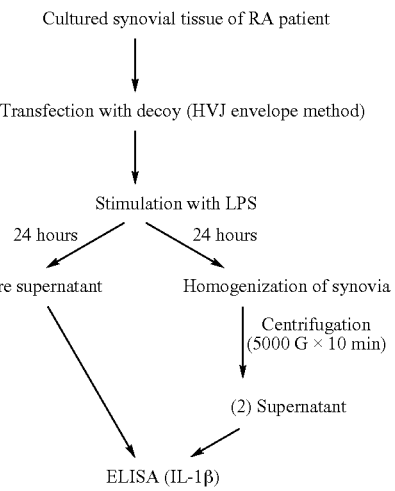

Example 2

Figure 3:
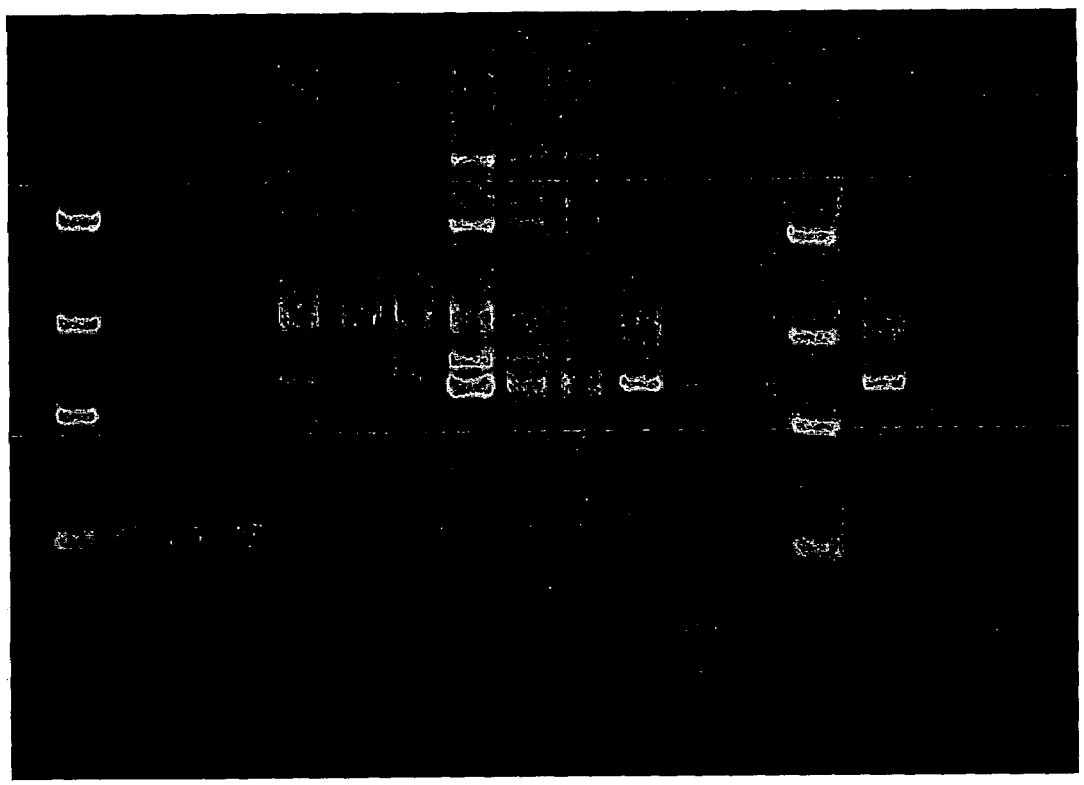
FIG. 3 is an electrophoretogram indicating the stability of a staple decoy.

B. Stability Test of Dumbbell Decoy (see FIG. 3)

Object: Comparison of tolerance in synovial fluid (as intact) between decoys

Sequences and Experimental Conditions:

1) Phosphorothioated double-stranded decoy

2) Phosphorothioated staple decoy

3) Non-phosphorothioated staple decoy (without S-modification)

4) Single-stranded decoy (a precursor of a staple oligonucleotide before ligation)

5) Phosphorothioate-terminated single-stranded decoy (a precursor of a staple oligonucleotide before ligation but after phosphorothioation at both terminals alone)

To each of these decoys was added the synovial fluid (as intact) to 0%, 50% or 100%, and the stabilities of the decoys were determined and compared by electrophoresis.

Result: In the synovial fluid, the phosphorothioated double-stranded decoy 1), the phosphorothioated staple decoy 2), and the non-phosphorothioated staple decoy 3) were stable; the single-stranded decoy 4) was almost stable; and the phosphorothioate-terminated signal-stranded decoy 5) was decomposed.

Specifically, the phosphorothioated double-stranded decoy 1) and the phosphorothioated staple decoy 2) were as stable in the 100% synovial fluid as in the 0% mixture (without addition of the synovial fluid).

The non-phosphorothioated staple decoy 3) decreased in stability depending on the concentration of the synovial fluid, but remained in a sufficient amount to be detected even in the 100% synovial fluid.

In contrast, the phosphorothioate-terminated single-stranded decoy 4) and the single-stranded decoy 5) showed lower stability in the synovial fluid as compared with the decoys 1) to 3).

In comparison between the phosphorothioate-terminated single-stranded decoy 4) and the single-stranded decoy 5), the phosphorothioate-terminated single-stranded decoy 4) showed a trace amount of stable decoy even in the 100% synovial fluid, but the single-stranded decoy 5) showed no stable decoy even in the 50% synovial fluid.

The invention claimed is:

1. A staple oligonucleotide consisting of the nucleotide sequence of SEQ ID NO: 1, which is a single-stranded oligonucleotide comprising a 5'-end sequence, an intermediate sequence and a 3'-end sequence, the 5'-end sequence having a reverse complementarity with the intermediate sequence, the 3'-end sequence having a reverse complementarity with the intermediate sequence and the intermediate sequence having loops at both ends, and wherein the loops do not form an intramolecular complementary bond.

2. The staple oligonucleotide according to claim 1, whose phosphate groups are not phosphorothioated.

3. The staple oligonucleotide according to claim 1, which is represented by the structural formula:

```
                  A                        A
            A   GGAGGGAAATCCCTTCAAGG    A
SEQ. 1      A   CCTCCCTTTA|GGGAAGTTCC   A
                  A                        A
``` wherein the vertical line is a non-binding site between the 5' end and the 3' end of the staple oligonucleotide.

* * * * *

UNITED STATES PATENT AND TRADEMARK OFFICE
CERTIFICATE OF CORRECTION

PATENT NO.        : 7,595,301 B2                                Page 1 of 1
APPLICATION NO.   : 10/568226
DATED             : September 29, 2009
INVENTOR(S)       : Kunugiza et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 507 days.

Signed and Sealed this

Fourteenth Day of December, 2010

David J. Kappos
*Director of the United States Patent and Trademark Office*